United States Patent
Jornod (10) Patent No.: US 8,496,595 B2
(45) Date of Patent: Jul. 30, 2013

(54) METHOD AND DEVICE FOR MEASURING THE PULSE BY MEANS OF LIGHT WAVES WITH TWO WAVELENGTHS

(75) Inventor: Alain Jornod, Neuchâtel (CH)

(73) Assignee: The Swatch Group Research and Development Ltd, Marin (CH)

( * ) Notice: Subject to any disclaimer, the term of this patent is extended or adjusted under 35 U.S.C. 154(b) by 336 days.

(21) Appl. No.: 12/875,804

(22) Filed: Sep. 3, 2010

(65) Prior Publication Data

US 2011/0054336 A1 Mar. 3, 2011

(30) Foreign Application Priority Data

Sep. 3, 2009 (EP) .................................... 09169391

(51) Int. Cl.
*A61B 5/024* (2006.01)

(52) U.S. Cl.
USPC ........... 600/508; 600/509; 600/527; 600/310; 600/311

(58) Field of Classification Search
USPC ........... 600/508, 509, 527, 310, 311; 342/115
See application file for complete search history.

(56) References Cited

U.S. PATENT DOCUMENTS

| | | |
|---|---|---|
| 4,770,179 A | 9/1988 | New, Jr. et al. |
| 5,595,176 A | 1/1997 | Yamaura |
| 6,993,378 B2 * | 1/2006 | Wiederhold et al. ......... 600/509 |
| 2005/0075553 A1 | 4/2005 | Sakai et al. |
| 2009/0278728 A1 * | 11/2009 | Morgan et al. ................ 342/115 |

FOREIGN PATENT DOCUMENTS

| | | |
|---|---|---|
| EP | 0 941 694 | 9/1999 |
| FR | 2 511 594 | 2/1983 |
| WO | 91/18550 | 12/1991 |
| WO | 96/12435 | 5/1996 |

OTHER PUBLICATIONS

European Search Report issued in corresponding application No. EP 09 16 9391, completed Feb. 10, 2010.

* cited by examiner

*Primary Examiner* — Christopher D Koharski
*Assistant Examiner* — Pamela M Bays
(74) *Attorney, Agent, or Firm* — Griffin & Szipl, P.C.

(57) ABSTRACT

System and method to determine the heartbeat of a person by a pulse measuring device. Light waves are generated in the direction of the skin by two light sources with a first wavelength ($\lambda_1$) which is sensitive to the pulse beat and movement of the person, and with a different second wavelength ($\lambda_2$) which is sensitive to movement, wherein a photodetector detects the reflected light waves. A pulse is determined based on calculation made of at least one non-coherent power spectrum on the basis of a spectral coherence function $\gamma$ which takes into account the dependence between the measurement signals relating to the first wavelength and to the second wavelength by the formula $S_{NC}=(1-\gamma^2)*S_{AA}$, where $S_{AA}$ is the average Fourier power spectrum of the signals relating to the first wavelength, and where $\gamma^2$ is between 0 and 1.

15 Claims, 7 Drawing Sheets

METHOD AND DEVICE FOR MEASURING THE PULSE BY MEANS OF LIGHT WAVES WITH TWO WAVELENGTHS

This application claims priority from European Patent Application No. 09169391.1 filed Sep. 3, 2009, the entire disclosure of which is incorporated herein by reference.

FIELD OF THE INVENTION

The invention relates to a method for measuring the pulse. This method makes it possible to determine the heartbeat or cardiac pulsation of a person on the basis of a useful signal extracted by means of the pulse measuring device carried by the person. In order to do this, the pulse measuring device in particular uses light waves with two different wavelengths.

The invention likewise relates to a device for measuring the pulse by means of light waves with two different wavelengths for implementing the method.

For the optical measurement of the modulation of the volume of blood vessels defining the heartbeat, there must be taken into account the fact that haemoglobin absorbs light more than other tissues at certain wavelengths. In order to do this, it is known to use two light beams with different wavelengths for measuring in particular the heartbeat or cardiac pulsation.

BACKGROUND OF THE INVENTION

Therefore, the U.S. Pat. No. 4,770,179 which describes an oximeter can be cited. This oximeter uses a first red LED diode and a second infrared LED diode in order to irradiate the blood vessels of a person and a photoreceptor, such as a photodiode, for sensing the reflected light. With this oximeter, a large error source of the optical signal by the modulation of said signal during movements of the person is observed. This modulation can be greater than the modulation of the optical absorption by the blood by a few orders of magnitude, which constitutes a disadvantage of such an oximeter. For this reason it does not make it possible to take into account the movements of the person in order to determine precisely the modulation of the volume of the blood vessels, i.e. the heartbeat.

In the same connection, the patent FR 2 511 594 which describes a device for controlling the pulse can be cited. This device comprises two infrared LED diodes, and a photodetector for measuring the cardiac pulsation of a sportsman when moving for example. However, precise differentiation between the pulse measurement of a person who is moving and a person in a stationary position is not provided. There is likewise not taken into account the fact that the absorption by the blood is more selective in wavelength than the modulation of the signal by the movements of the person in order to make it possible to effect the pulse measurement. Furthermore, equally nothing is provided for suppressing the effect of ambient light which is another source of error for the pulse measurement.

One solution to the problem of the pulse measurement connected to the movement of the person is proposed in the patent application US 2005/0075553. This patent application describes a method and a portable device, such as a wristwatch, for managing biological information, such as heartbeat and functions of the nervous system. The wristwatch comprises a sensor device having an LED diode of a green colour, an infrared LED diode and a photodiode for sensing the light reflected by the skin and the blood vessels and which originates from the LED diodes which are switched on alternately, and a microcontroller unit connected to the sensor device in order to control it. The green light waves make it possible to obtain a signal for detecting the pulse beat and movement whilst the infrared light waves make it possible essentially to obtain a signal from the movement of the person wearing the watch.

The microcontroller unit receives digital signals from an analogue/digital converter of the sensor device. This unit effects a fast Fourier transformation (FFT) of the digital signals received from the green and infrared light waves. After standardisation of the Fourier spectra, the spectrum of the infrared light waves is subtracted from the spectrum of the green light waves in order to be able to remove the effect of the movement and to calculate the pulse of the person. However, the intensity of the light waves must be well adapted in order to allow complete removal of the effect of the movement after the operation of subtracting the Fourier spectra of the light waves, which is a disadvantage. Furthermore, high electrical consumption is observed in effecting the pulse measurement which constitutes another disadvantage.

SUMMARY OF THE INVENTION

The object of the invention is therefore to remedy the disadvantages of the prior art mentioned above by providing a method for determining the heartbeat of a person by means of a pulse measuring device, which makes it possible to determine the pulse easily without being dependent upon the intensity of the generated and sensed light waves.

To this end, the invention relates to a method for determining the heartbeat of a person by means of a pulse measuring device, which comprises a first light source for emitting light waves with a first wavelength, a second light source for emitting light waves with a second wavelength, and a photodetector for sensing the light reflected by the tissues of the skin and the blood vessels and for providing measurement signals to a microcontroller unit, the first and second wavelengths being different and determined so that the light waves with the first wavelength are sensitive to the pulse beat and to the movement of a person, and so that the light waves with the second wavelength are sensitive to movement, wherein the method comprises the steps of:
  generating light waves with the first wavelength and the second wavelength by means of the first and second light sources, and transmitting them in the direction of the skin of the person,
  detecting the light waves with the first and second wavelengths which are reflected by the tissues of the skin and the blood vessels in order to provide electrical measurement signals,
  calculating at least one non-coherent power spectrum on the basis of a spectral coherence function $\gamma$ which takes into account the dependence between the measurement signals relating to the first wavelength and to the second wavelength by the formula $S_{NC}=(1-\gamma^2)\cdot\overline{S_{AA}}$, where $\overline{S_{AA}}$ is the average Fourier power spectrum of the measurement signals relating to the first wavelength of the sensed light waves and where $\gamma^2$ is between 0 and 1, and
  determining the heartbeat of the person by means of the non-coherent power spectrum.

Particular steps of the method for determining the heartbeat are defined in the dependent claims 2 to 7.

One advantage of the method according to the invention resides in the fact that a spectral coherence function applied to the measurement signals provided by the detector is calculated. The coherence function makes it possible to distinguish effectively the contributions of the heartbeat and the movement of the person. From this coherence function it is thus possible to determine an average non-coherent power spectrum from which it is easy to extract the useful pulse beat signal. The light intensity difference sensed by the detector has therefore no longer any need to be precisely regulated.

Another advantage of the method according to the invention resides in the fact that it is likewise possible to extract a useful signal for the movement of the person on the basis of an average coherent power spectrum. The frequency of the movement of the person can thus be determined thanks to this average coherent power spectrum.

To this end, the invention likewise relates to a pulse measuring device which is suitable for implementing the method for determining the heartbeat of a person, said device comprising an optical detection unit which comprises a first light source for emitting light waves with a first wavelength, a second light source for emitting light waves with a second wavelength, and a photodetector for sensing the light reflected by the tissues of the skin and the blood vessels and for providing measurement signals to a microcontroller unit, wherein the microcontroller unit comprises at least one processing unit which is able to calculate at least one non-coherent power spectrum on the basis of a spectral coherence function γ which takes into account the dependence between the measurement signals provided by the photodetector and relating to the first wavelength and to the second wavelength in order to determine the heartbeat of the person by means of the non-coherent power spectrum.

Particular embodiments of the pulse measuring device are defined in the dependent claims 9 to 11.

To this end, the invention likewise relates to a portable electronic instrument, such as a wristwatch equipped with a pulse measuring device, wherein the first and second light sources are disposed in a case of the instrument for providing the light waves through a base of the case, and wherein the photodetector is provided in order to sense the light waves reflected through an opening or transparent portion of the base of the case.

BRIEF DESCRIPTION OF THE DRAWINGS

The objects, advantages and features of the method for determining the heartbeat of a person and of the device for its implementation will appear more clearly in the following description of at least one embodiment of the invention in conjunction with the drawings in which.

DETAILED DESCRIPTION OF THE PREFERRED EMBODIMENTS

In the following description, all the elements of the pulse measuring device which are well known to the person skilled in the art in this technical field will be referred to only in a simplified manner, in particular with respect to the microcontroller unit for processing digital signals in conjunction with detected light waves. The pulse measuring device can be integrated in a portable electronic instrument which is able to be in contact with the skin of the wearer, such as a wristwatch or a portable telephone or a badge or another instrument.

Figure 1:
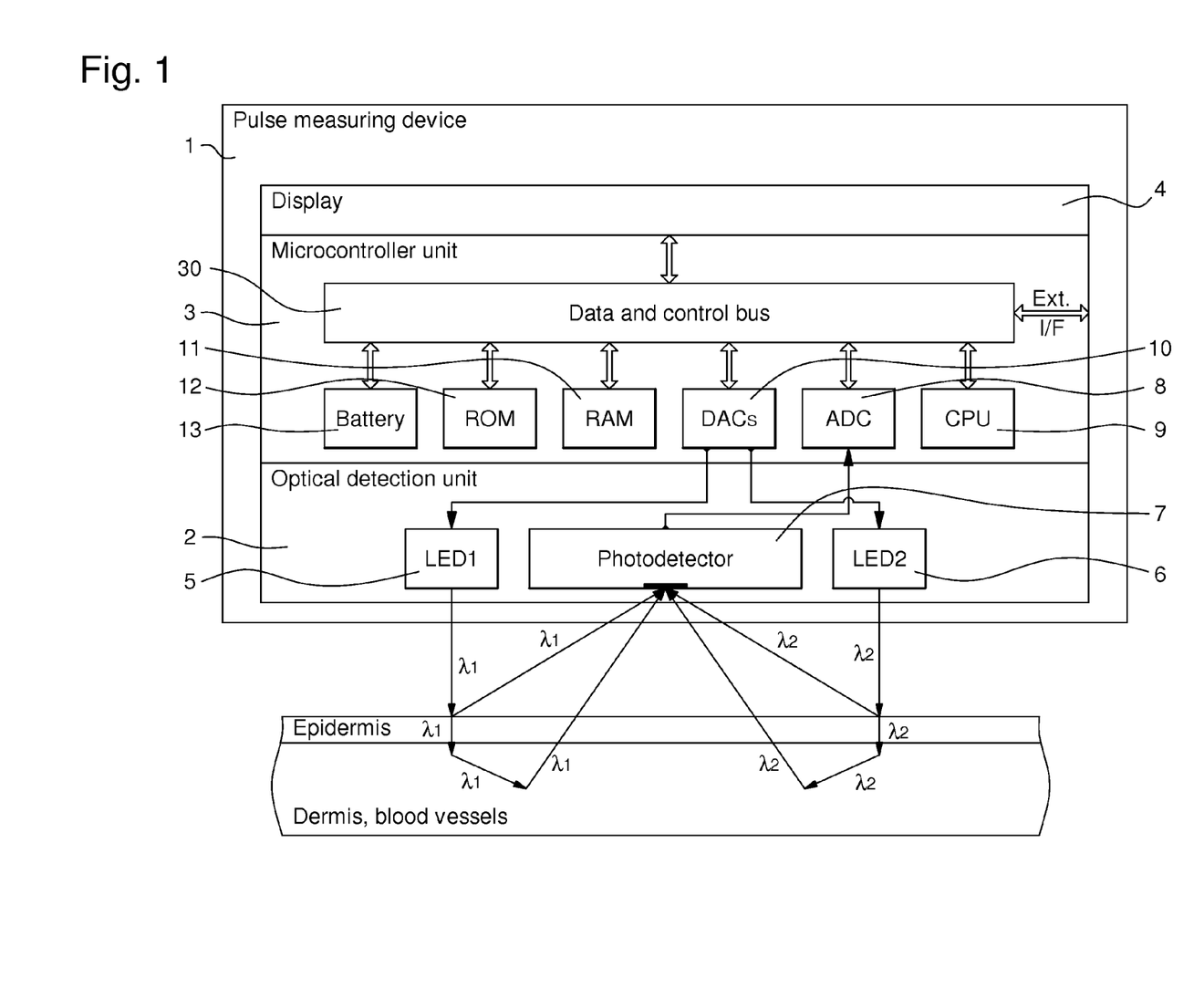
FIG. 1 represents a block diagram of the various components of the pulse measuring device for implementation of the method according to the invention.

In FIG. 1, a pulse measuring device 1 is represented. This device comprises an optical detection unit 2, which consists generally of two light sources, such as two electroluminescent LED diodes 5 and 6, and a photodetector 7 which comprises at least one photodiode. The LED diodes each emit light waves having a different wavelength. A first LED diode 5 produces light waves with a first wavelength $\lambda_1$ preferably situated in the green range, whilst a second LED diode 6 produces light waves with a second wavelength $\lambda_2$ preferably situated in the red or infrared range.

The pulse measuring device 1 also comprises a microcontroller unit 3 and a display cell 4. This display cell is connected to the microcontroller unit 3 by means of a data and control bus 30 of the unit, which likewise connects various components of the microcontroller unit 3. The display cell 4 can be a liquid crystal device for example or another type so as to be able to display, when requested by the user, information relating to the pulse measurement. The display cell controlled by the microcontroller unit can display information about the pulse measurement continuously during the pulse measurement or after having been stored in the memory means at any time after the pulse measurement. A plurality of pulse values can thus be stored and displayed on the display cell when requested.

The microcontroller unit is firstly composed of a supply source, which is defined such as a battery 13 for supplying all the components of the pulse measuring device. This microcontroller unit also comprises a digital-analogue converter 10 for providing activation signals respectively to each LED diode 5 and 6 following a digital command provided by a processing unit 9, such as a processor. The microcontroller unit likewise comprises an analogue-digital converter 8 for receiving the measurement signals sensed by the photodetector 7 and for converting them digitally for processing operations in the processing unit 9. The microcontroller unit also comprises memory means, which are defined for example such as a ROM type memory 12 and a RAM type memory 11. The ROM memory 12 comprises all the instructions for operating the microcontroller unit and specific configuration parameters. The RAM type memory 11 is intended to store, in particular during operation of the pulse measuring device, parameters drawn from the digital signals provided by the photodetector 7 and processed in the processing unit 9.

The microcontroller unit 3 can also comprise an oscillator stage, not represented, which can be dependent upon a quartz resonator, not represented. In the case of use in a wristwatch, said microcontroller unit can comprise part of the oscillator stage, which is intended for the time base of said watch. In this case, this oscillator stage is provided with a plurality of dividers for providing clock signals for all the operations processed by the processing unit 9 of the microcontroller unit 3.

During normal operation of the pulse measuring device 1 during a determined measuring period, the LED diodes 5 and 6 are switched on alternately and discontinuously in time under the control of the processing unit 9. The first LED diode 5, which provides light waves with the first wavelength $\lambda_1$, is switched on successively in time during determined periods of time. The second LED diode 6, which provides light waves at the second wavelength $\lambda_2$, is switched on successively in time during determined periods of time, which generally correspond to the activation periods of time of the first LED diode. When one of the LED diodes is switched on, the other LED diode is generally switched off and vice versa whilst leaving temporal intervals where both LED diodes are switched off.

Figure 7:
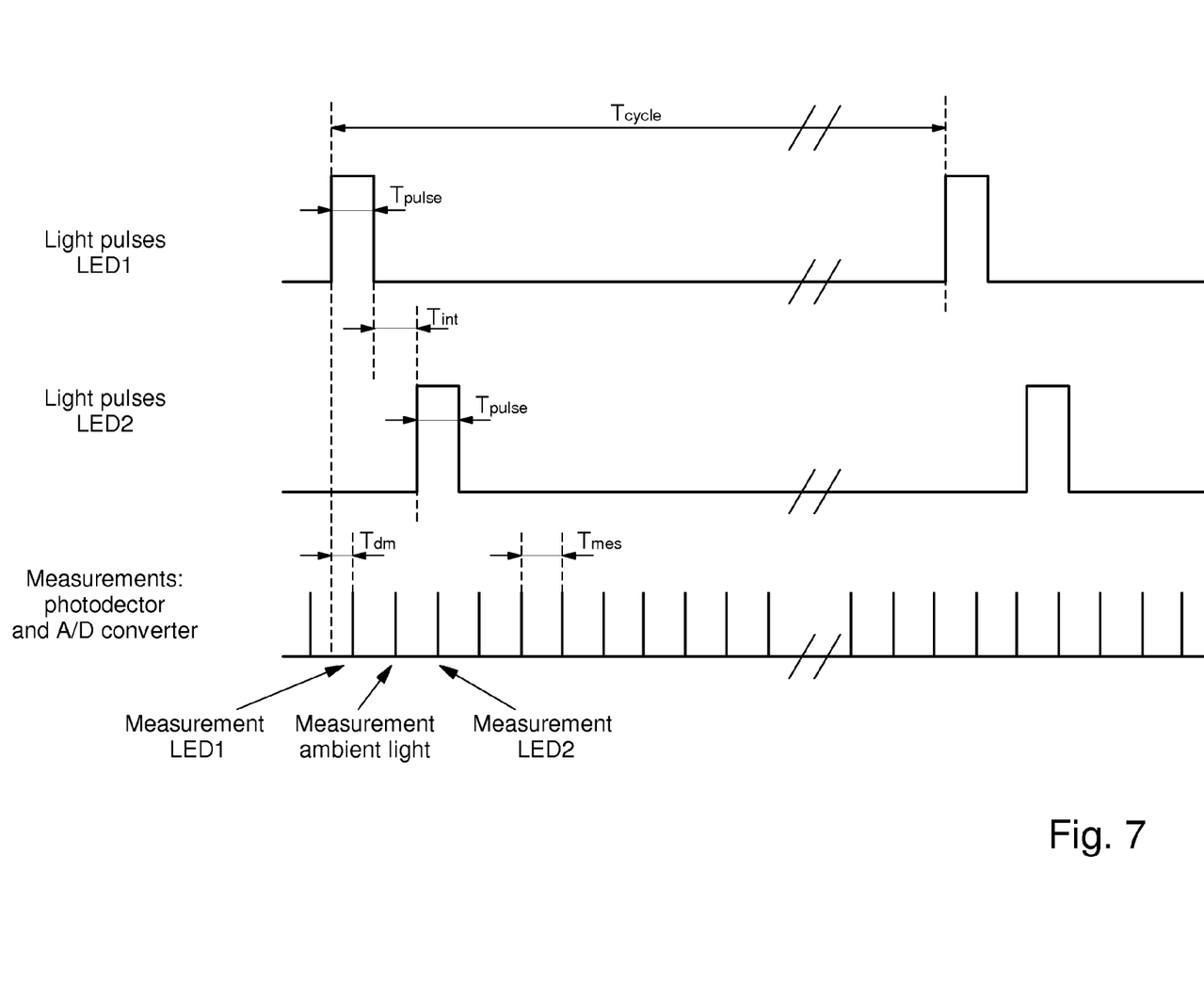
FIG. 7 represents temporal graphs of the light pulses generated by the light sources and the measurements effected by the photodetector and the analogue-digital converter of the pulse measuring device according to the invention.

By way of non-limiting example, temporal graphs of the light waves generated by the light sources and the measurement signals by means of the photodetector and the analogue-digital converter are represented in FIG. 7. The LED diodes can be switched on alternately and discontinuously in time. The first diode LED1 is switched on first during a determined period of time $T_{pulse}$ which in this case can be of the order of 20 μs. The second diode LED2 is switched on a pause time interval $T_{int}$ for example of the order of 20 μs after switching off the first diode LED 1. The activation time period of the second diode LED2 is similar to that of the first diode LED1. The light pulses of each LED diode occur after each cycle $T_{cycle}$ which can be of the order of 1 ms. Measurements of the sensed light waves of the first diode LED1, of ambient light and of the second diode LED2 are effected at determined measurement periods $T_{mes}$ which can be of the order of 20 μs, but with a time shift $T_{dm}$ of 10 μs relative to each activation of the LED diodes.

It should be noted that instead of a temporal modulation represented in particular in FIG. 7, effecting a modulation in frequency could also have been provided. In this case, the signals of the first diode LED1 are emitted and detected at a frequency of the order of 600 Hz, whilst those of the second diode LED2 are emitted and detected at a frequency of the order of 900 Hz. With that, a frequency modulation and demodulation is effected.

For the method for determining the heartbeat, the pulse measuring device 1 can be set in operation by an external command, such as by means of a button of a portable electronic instrument in which it is placed. The pulse measuring device can likewise be set in operation by automatic programming. In these conditions, it may be required that a pulse measurement and a calculation of the frequency of the movement of the person occur in programmed temporal periods which are sufficiently spaced from each other.

The first wavelength $\lambda_1$, which is typically in green, is chosen to correspond to a greater optical absorption by haemoglobin than the second wavelength $\lambda_2$ which is typically in red. The measurement signals originating from the photodetector 7 which has sensed the light waves reflected and/or absorbed in part by the haemoglobin are recorded. This recording, in particular in the RAM memory 11, can be effected directly after digitalisation of the measurement signals by the analogue-digital converter 8. This recording operates continuously whilst taking into account the temporal intervals where the two light sources are switched off.

In the pause temporal intervals, it is provided in particular that the processing unit 9 takes into account the ambient light sensed by the photodetector 7. This makes it possible to remove the effect of the ambient light during measurement of the pulse. To this end, an average value of the light detected when the light sources 5 and 6 are switched off, i.e. the detected ambient light, can be subtracted continuously in the temporal range before a transformation into the frequency range. It can likewise be imagined that the spectrum of the ambient light is subtracted from the spectra of the light waves with two wavelengths $\lambda_1$ and $\lambda_2$ in the Fourier frequency range.

It should be noted that the configuration parameters Ext can be provided externally by means of the data and control bus 30. In particular measurement information I/F can again be transmitted by means of the data and control bus 30 to the exterior of the pulse measuring device 1.

The method for determining the heartbeat of the present invention can use the spectral coherence function in particular in the processing unit 9 which can be a processor. This method makes it possible to extract a useful pulse beat signal by means of the pulse measuring device 1. This function is a measure of the degree of dependence between two signals A and B in the frequency range. The two signals A and B can be considered as the two signals provided by the photodetector. These signals A and B correspond respectively to the sensed light waves with the first wavelength $\lambda_1$ and to the sensed light waves with the second wavelength $\lambda_2$. The function γ is calculated according to a temporal average of the Fourier spectra of the signals A and B. This function γ takes values between 0, for which no relation exists between the two signals, and 1, for which there is a perfect linear relation. This function γ is defined by the following function:

$$\gamma^2 = \frac{|\overline{S_{AB}}| \cdot |\overline{S_{AB}}|}{\overline{S_{AA}} \cdot \overline{S_{BB}}}$$

where $\overline{S_{AA}} = FFT(A) \cdot FFT^*(A)$ and $\overline{S_{BB}} = FFT(B) \cdot FFT^*(B)$ are respectively the power spectra of the signals A and B and $\overline{S_{AB}} = FFT(A) \cdot FFT^*(B)$ is the average of the intersected Fourier spectra of signals A and B.

The spectral coherence function γ is normally used to determine the coherent spectral power $S_{CO} = \gamma^2 \cdot \overline{S_{BB}}$, which represents the coherent part between the two signals A and B which is not affected by the non-coherent part, represented essentially by noise. This spectral function γ can also be used to calculate the signal/noise ratio of a system $S/N = \gamma^2/(1-\gamma^2)$.

For the method of the present invention and as indicated previously, the two signals A and B are considered as responses to the wavelengths $\lambda_1$ and $\lambda_2$. The contributions of the movement are presented in the signals A and B. They therefore represent the coherent part of the Fourier spectra. The modulation of the optical signals by the blood beat, which is essentially contained in the signal A, represents for its part the non-coherent part of the spectrum of the signal A with that of the signal B. The function, which contains most information relating to the pulse beat, is therefore the non-coherent spectral power given by the following formula:

$$S_{NC} = (1-\gamma^2) \cdot \overline{S_{AA}}$$

It is from this function that the microcontroller unit 3, in particular by means of the processor, must extract the useful signal, the pulse beat frequency determining the pulse of the person.

Using a method for determining the pulse beat in the presence of modulation connected to movements, which is based on the response differences of the tissue as a function of the wavelength of the light, could equally have been envisaged. This determination method can use a standardisation factor in the Fourier range between the spectra of the two wavelengths $\lambda_1$ and $\lambda_2$ as in the state of the art. In order to do this, the standardisation factor between the spectra of $\lambda_1$ and $\lambda_2$ is calculated in the upper frequencies of the Fourier spectrum, where the spectral content is dominated by the modulation of the signal connected to movement. The standardisation factor can be an RMS value of the spectrum in a range between two frequencies, which are typically 6 and 10 Hz.

Once the standardisation has been effected, the spectrum of the second wavelength $\lambda_2$ is subtracted from that of the first wavelength $\lambda_1$. The modulation of the optical signals via movements is similar for the two wavelengths. The main part of the spectrum due to vibrations or movements is therefore eliminated by subtraction. This subtraction reduces, but in a non-determinant manner, the amplitude of the modulated signal. In the example where the modulation of the optical signals by the blood beat is ten times greater for the first wavelength $\lambda_1$ than for the second wavelength $\lambda_2$, the reduction in pulse beat signal after the subtraction operation is only 10%.

In order to understand better the shape of the signals sensed in time and also the spectra calculated by the pulse measuring device, reference can be made to FIGS. 2 to 6 described hereafter.

Figure 2:
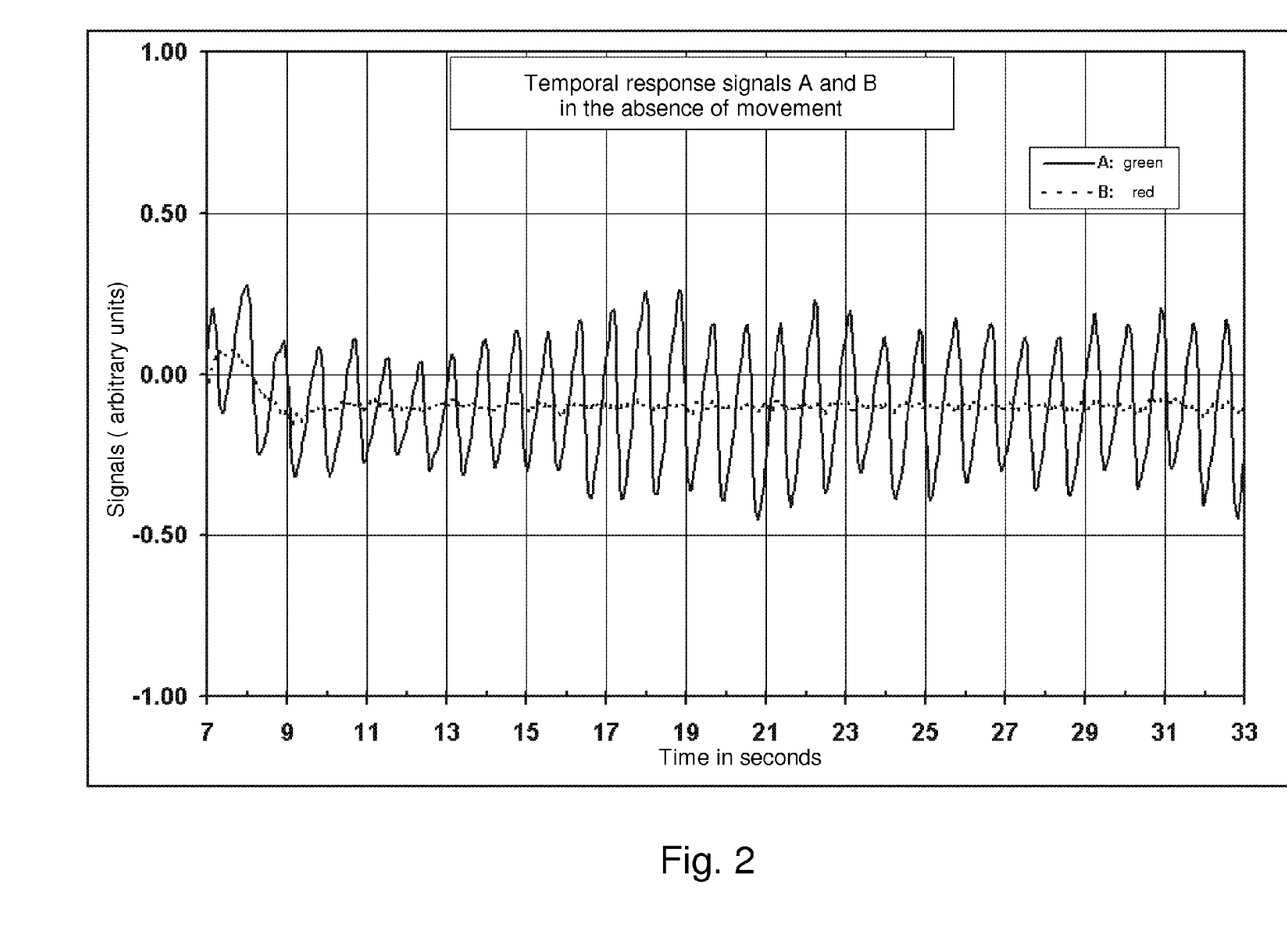
FIG. 2 represents a temporal graph of the signals with two wavelengths sensed by the photodetector of the pulse measuring device according to the invention without movement of the wearer of the device.

In FIG. 2, there is represented firstly the signals A and B in time sensed by the photodetector, originating from the light waves emitted by the two LED diodes at the first wavelength $\lambda_1$ (A) and at the second wavelength $\lambda_2$ (B). There is noted on this graph in bold the signals sensed by the photodetector relating to the first wavelength and in broken lines those sensed by the photodetector relating to the second wavelength in the absence of movement of the person who is carrying said device.

Normally, these signals are shifted in time relative to each other being given the alternate and discontinuous activation of the LED diodes used for this pulse measurement. As the signals at the first wavelength in green are sensitive to the pulse beat, only a view of the pulse beat by the light waves at the first wavelength $\lambda_1$ is represented, i.e. approx. 3 cycles in 2 seconds (1.5 Hz), because little fluctuation is observed for the light waves with the second wavelength $\lambda_2$.

Figure 3:
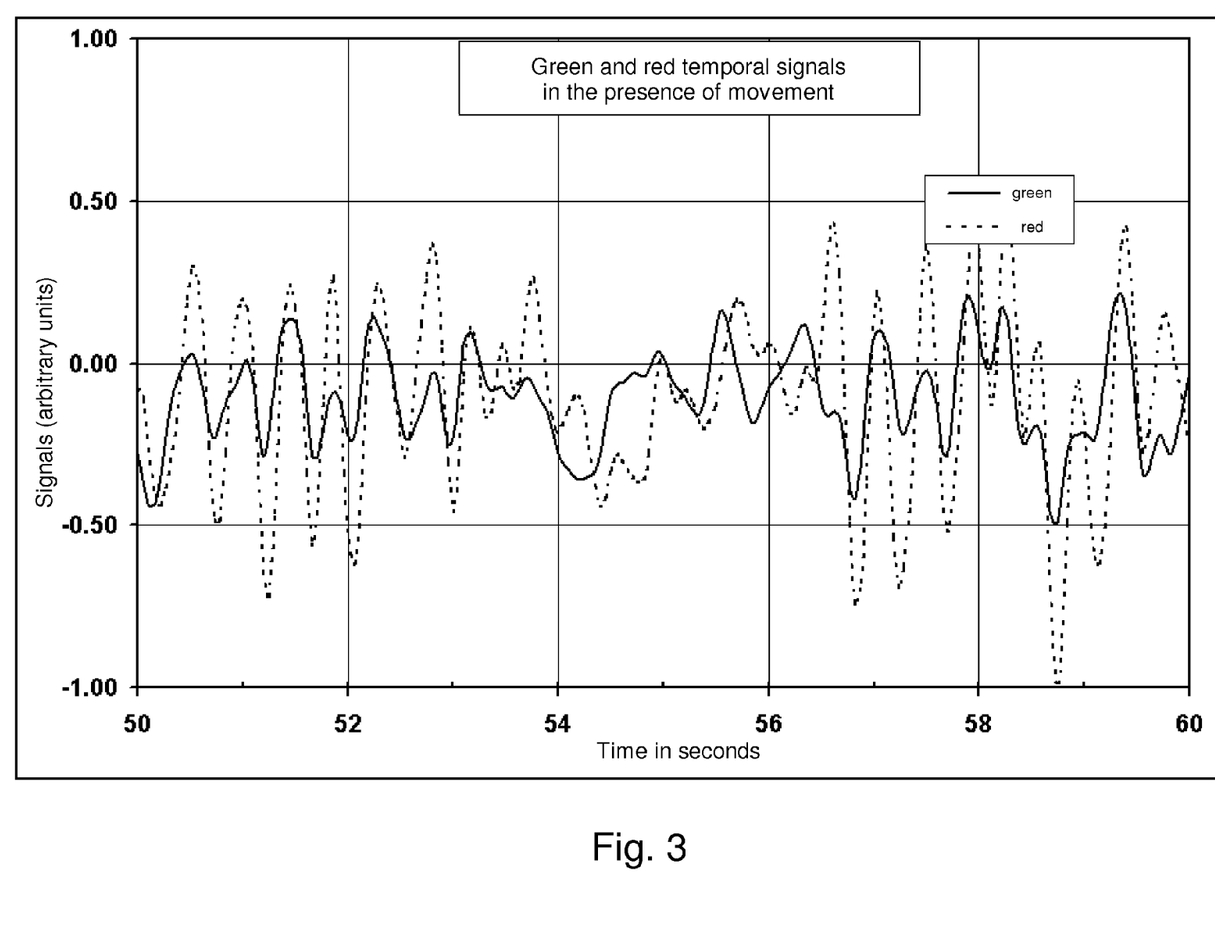
FIG. 3 represents a temporal graph of the signals with two wavelengths sensed by the photodetector of the pulse measuring device according to the invention in the presence of movement of the wearer of the device.

In FIG. 3 there are represented, in the presence of movement of the wearer of the device, signals A and B in time sensed by the photodetector originating mainly from light waves emitted by the two LED diodes. These light waves are reflected and/or absorbed by the haemoglobin before being sensed by the photodetector. It is noted this time that the pulse beat is represented much less clearly on said signals A and B provided by the photodetector.

Figure 4:
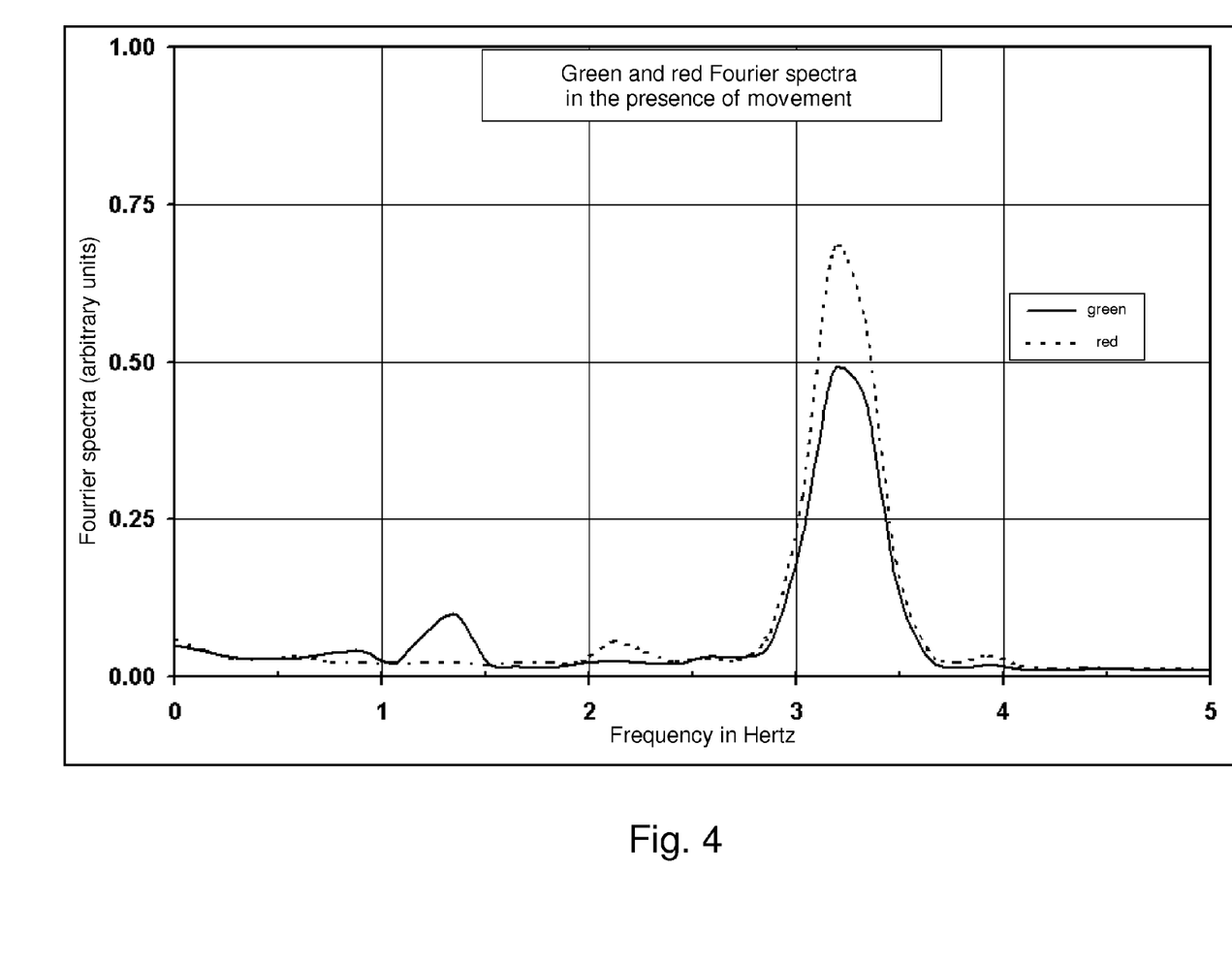
FIG. 4 represents a graph of the Fourier spectra of the signals with two wavelengths sensed by the photodetector of the pulse measuring device according to the invention in the presence of movement of the wearer of the device.

In FIG. 4, there are represented the Fourier spectra of the signals A and B provided by the photodetector on the basis of light waves with two sensed wavelengths. The Fourier spectra of the signals A and B are obtained as a function of the signals A and B in the temporal range, which have been recorded as represented in FIG. 3. There is noted in FIG. 4 the contribution due to movement at approx. 3.2 Hz of the signals A and B, whilst the pulse beat is situated at approx. 1.3 Hz and is visible only for the signals A at the first wavelength.

Figure 5:
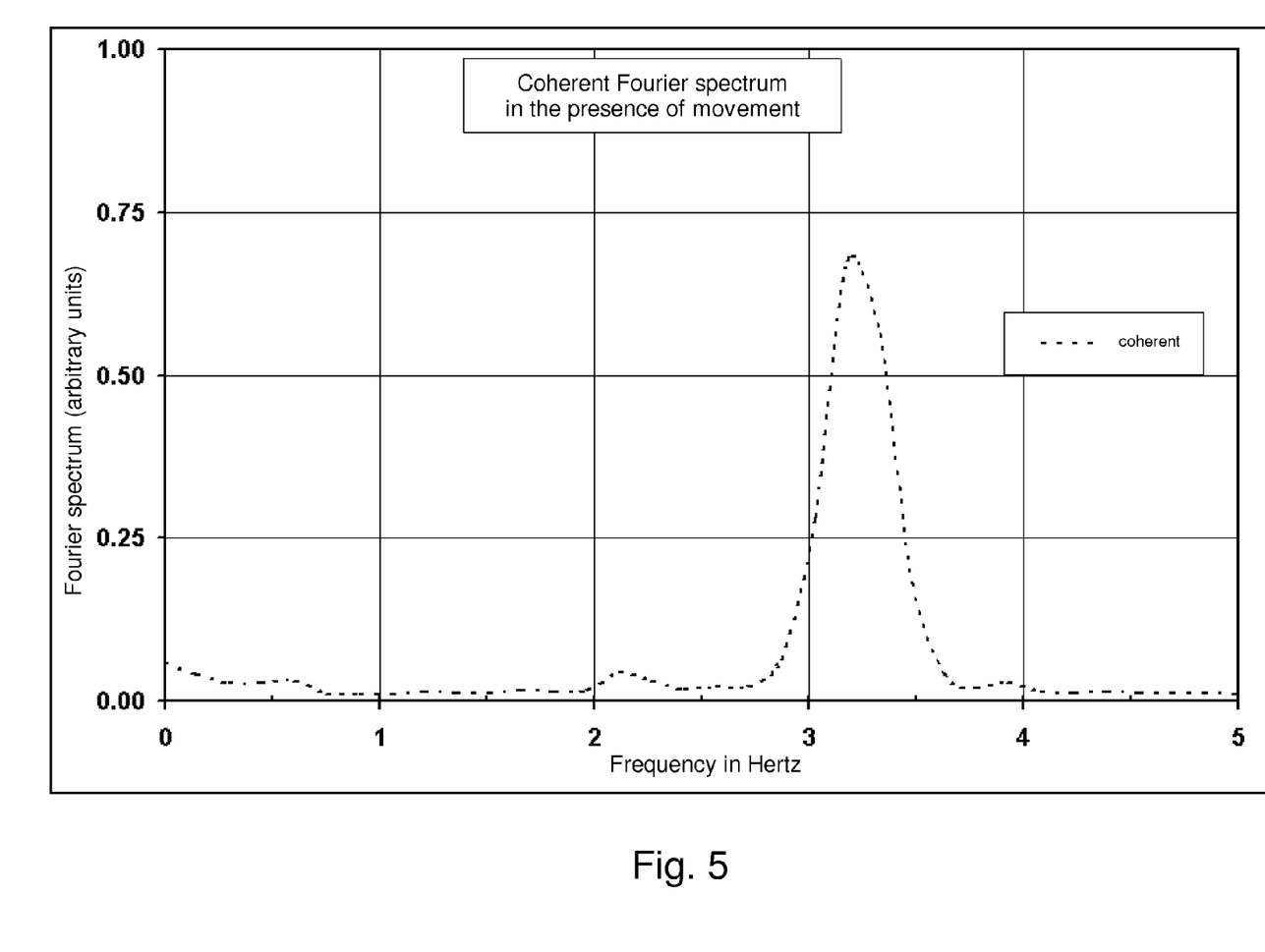
FIG. 5 represents a graph of the coherent Fourier power spectrum in the presence of movement of the signals sensed by the photodetector of the pulse measuring device according to the invention.

In FIG. 5 there is represented only the coherent Fourier power spectrum of the signals A and B provided by the photodetector on the basis of the sensed light waves with two wavelengths. This coherent power spectrum is obtained as a function of the signals A and B in the temporal range as represented in FIG. 3.

Figure 6:
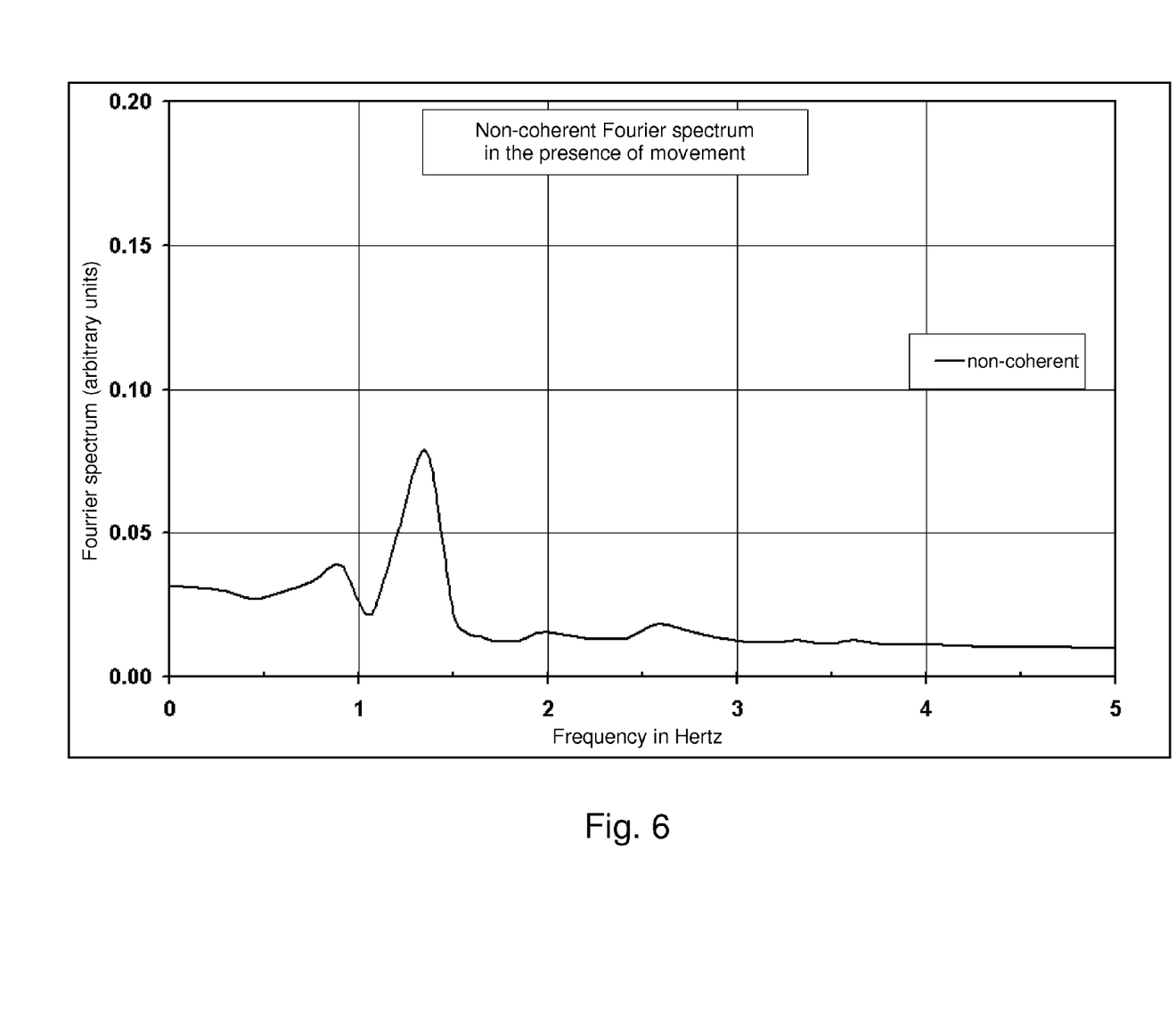
FIG. 6 represents a graph of the non-coherent Fourier power spectrum in the presence of movement of the signals sensed by the photodetector of the pulse measuring device according to the invention.

Finally in FIG. 6, there is represented only the non-coherent Fourier power spectrum of the signals A and B provided by the photodetector on the basis of the sensed light waves with two wavelengths. This non-coherent power spectrum is obtained as a function of the signals A and B in the temporal range as represented in FIG. 3.

In FIGS. 5 and 6, it is established that the contributions of the movement and of the pulse beat are clearly differentiated. The component of movement at approx. 3.2 Hz appears clearly only on the coherent spectrum of FIG. 5, whilst the pulse beat component at approx. 1.3 Hz appears clearly only on the non-coherent spectrum of FIG. 6. In these conditions, it is easy for the processing unit of the microcontroller unit to extract the useful heartbeat signal directly from the non-coherent power spectrum represented in FIG. 6. Of course said processing unit can likewise be in a position to determine the frequency of movement of the person carrying said pulse measuring device on the basis of the coherent power spectrum as represented in FIG. 5.

From the description which has just been given, several variants of the method and of the pulse measuring device can be designed by the person skilled in the art without going beyond the scope of the invention defined by the claims. It can be imagined to switch on the two light sources at the same time, and to perform a wavelength selection at the level of the photodetector. The pulse measuring device can be integrated in a wristwatch with the light sources and the photodetector disposed at the side of the bottom of the case of the watch in direct contact with the skin of the wearer. Emission of the light waves and sensing of the reflected light waves are effected through one or more openings or transparent portions of the bottom of the case.

What is claimed is:

1. A method for determining a pulse of a person with a pulse measuring device wherein the pulse measuring device comprises a first light source adapted to generate light waves having a first wavelength, a second light source adapted to generate light waves having a second wavelength, and a photodetector disposed to sense light reflected by skin tissue and blood vessels and operably connected to provide measurement signals to a microcontroller unit, wherein the first and second wavelengths are different and determined so that the light waves with the first wavelength are sensitive to a pulse beat and to a movement of the person, and so that the light waves with the second wavelength are sensitive to movement, wherein the method comprises the steps of:
   (a)—generating light waves with the first wavelength by the first light source and generating light waves with the second wavelength by the second light source, and transmitting both light waves in a direction of the skin of the person;
   (b)—detecting, using the photodetector, light waves of the first and second wavelengths reflected by the skin tissue and blood vessels and providing measurement signals to the microcontroller unit;
   (c)—calculating, using the microcontroller unit, at least one non-coherent power spectrum on the basis of a spectral coherence function $\gamma$, wherein the spectral coherence function $\gamma$ accounts for the dependence between the measurement signals relating to the first wavelength and to the second wavelength by the formula $S_{NC}=(1-\gamma^2)\cdot\overline{S_{AA}}$, where $\overline{S_{AA}}$ is the average Fourier power spectrum of the measurement signals relating to the first wavelength of the sensed light waves and where $\gamma^2$ is between 0 and 1; and
   (d)—determining the pulse of the person by the non-coherent power spectrum.

2. The method for determining the pulse of a person using the pulse measuring device according to claim 1, wherein the calculating step further comprises calculating at least one coherent power spectrum on the basis of a spectral coherence function γ, by the formula $S_{NC}=(1-\gamma^2)\cdot\overline{S_{AA}}$, where $\overline{S_{AA}}$ is the average Fourier power spectrum of the measurement signals relating to the second wavelength of the sensed light waves and where $\gamma^2$ is between 0 and 1, and wherein the frequency of the movement of the person is determined by the coherent power spectrum.

3. The method for determining the pulse of a person according to claim 1, wherein the generating step further comprises switching on the light sources to alternately generate light waves with the first and second wavelengths.

4. The method for determining the pulse of a person according to claim 3, wherein generating step further comprises switching on the light sources alternately and discontinuously during determined periods of time, and wherein the light sources are th switched off during temporal intervals between each alternate switching on of the light sources.

5. The method for determining the pulse of a person according to claim 4, further comprising calculating an average value of light detected by the photodetector when the light sources are switched off and subtracting the average value continuously before a transformation into a frequency range in the microcontroller unit.

6. The method for determining the pulse of a person according to claim 3, wherein the pulse measuring device is set in operation manually or automatically during a determined measuring period.

7. The method for determining the pulse of a person according to claim 6, wherein the pulse measuring device is set in operation automatically by a programmed temporal period of several orders of magnitude greater than each determined measuring period.

8. The method for determining the pulse of a person according to claim 4, wherein the pulse measuring device is set in operation manually or automatically during a determined measuring period.

9. The method for determining the pulse of a person according to claim 5, wherein the pulse measuring device is set in operation manually or automatically during a determined measuring period.

10. A pulse measuring device, comprising
   (a) an optical detection unit, including,
      (i)—a first light source adapted to generate light waves with a first wavelength;
      (ii) a second light source adapted to generate light waves with a second wavelength; and
      (iii) a photodetector disposed to sense light reflected by a person's skin tissue and blood vessels and operably connected to provide measurement signals; and
   (b) a microcontroller unit, operably connected to the photodetector, and including, at least one processing unit adapted to calculate at least one non-coherent power spectrum on the basis of a spectral coherence function γ, wherein the spectral coherence function γ accounts for the dependence between the measurement signals provided by the photodetector, and relating to the first wavelength and to the second wavelength, by the formula $S_{NC}=(1-\gamma^2)\cdot\overline{S_{AA}}$, where $\overline{S_{AA}}$ is the average Fourier power of the measurement signals relating to the first wavelength of the sensed light waves and where $\gamma^2$ is between 0 and 1 in order to determine the pulse or a frequency of movement or the pulse and the frequency of movement of the person by the non-coherent power spectrum.

11. The pulse measuring device according to claim 10, wherein the microcontroller unit further comprises a memory, wherein the memory stores instructions for setting the microcontroller unit in operation, configuration parameters that are specific to the unit, and data relating to the digitalised measurement signals provided by the photodetector and processed by the processing unit, and wherein the processing unit is able to calculate at least one coherent power spectrum on the basis of the spectral coherence function γ in order to determine the frequency of the movement of the person.

12. The device for measuring the pulse according to claim 10, wherein the device further comprises:
   (c) a display cell controlled by the microcontroller unit, and operably connected to display information relating to the pulse or to the frequency of movement or to the pulse and the frequency of movement of the person carrying the device.

13. The device for measuring the pulse according to claim 10, wherein the microcontroller unit comprises an analogue-digital converter for digitally converting the measurement signals provided by the photodetector to be processed by the processing unit, and at least one digital-analogue converter for alternating control, on the basis of control signals from the processing unit, of the activation of each light source, each light source being an electroluminescent diode.

14. A portable electronic instrument that comprises a pulse measuring device according to claim 10, wherein the first and second light sources are disposed in a case of the instrument for providing the light waves through a base of the case, and wherein the photodetector is provided in order to sense the light waves reflected through an opening or transparent portion of the base of the case.

15. The portable electronic instrument according to claim 14, wherein the portable electronic instrument is a wristwatch.

* * * * *